US010688071B2

(12) United States Patent
Loupenok

(10) Patent No.: US 10,688,071 B2
(45) Date of Patent: *Jun. 23, 2020

(54) TOPICAL FOAM COMPOSITION

(75) Inventor: Leon Loupenok, Rowville (AU)

(73) Assignee: MAYNE PHARMA LLC, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/553,036

(22) Filed: Jul. 19, 2012

(65) Prior Publication Data

US 2013/0005774 A1 Jan. 3, 2013

Related U.S. Application Data

(63) Continuation of application No. 12/711,337, filed on Feb. 24, 2010.

(60) Provisional application No. 61/202,403, filed on Feb. 25, 2009.

(51) Int. Cl.
A61K 31/4436 (2006.01)
A61P 17/00 (2006.01)
A61K 31/203 (2006.01)
A61K 9/00 (2006.01)
A61K 9/107 (2006.01)
A61K 9/12 (2006.01)
A61K 31/192 (2006.01)
A61K 45/06 (2006.01)
A61K 31/00 (2006.01)

(52) U.S. Cl.
CPC .......... *A61K 31/203* (2013.01); *A61K 9/0014* (2013.01); *A61K 9/1075* (2013.01); *A61K 9/122* (2013.01); *A61K 31/00* (2013.01); *A61K 31/192* (2013.01); *A61K 31/4436* (2013.01); *A61K 45/06* (2013.01); *Y10S 514/938* (2013.01); *Y10S 514/939* (2013.01); *Y10S 514/941* (2013.01); *Y10S 514/945* (2013.01)

(58) Field of Classification Search
CPC . A61K 31/192; A61K 31/4436; A61K 9/0014
USPC .................................................. 424/45, 401
See application file for complete search history.

(56) References Cited

U.S. PATENT DOCUMENTS

| 4,985,250 | A | * | 1/1991 | Bee et al. ...................... 424/401 |
| 5,026,548 | A | * | 6/1991 | Evans et al. ................... 424/750 |
| 5,968,528 | A | | 10/1999 | Deckner et al. |
| 6,333,362 | B1 | | 12/2001 | Lorant |
| 6,358,541 | B1 | | 3/2002 | Goodman |
| 6,511,655 | B1 | * | 1/2003 | Muller et al. ................... 424/59 |
| 6,607,733 | B1 | | 8/2003 | Diec et al. |
| 6,730,288 | B1 | | 5/2004 | Abram |
| 7,115,277 | B2 | | 10/2006 | Firestone et al. |
| 7,141,237 | B2 | * | 11/2006 | Abram et al. ................... 424/45 |
| 7,326,408 | B2 | | 2/2008 | Angel et al. |
| 7,387,807 | B2 | | 6/2008 | Callaghan et al. |
| 8,808,716 | B2 | * | 8/2014 | Loupenok ............ A61K 9/0014 424/401 |
| 2004/0115257 | A1 | * | 6/2004 | Firestone et al. .............. 424/452 |
| 2005/0014729 | A1 | | 1/2005 | Pulaski |
| 2005/0031547 | A1 | | 2/2005 | Tamarkin et al. |
| 2005/0042173 | A1 | | 2/2005 | Besse et al. |
| 2005/0069566 | A1 | | 3/2005 | Tamarkin et al. |
| 2005/0074414 | A1 | | 4/2005 | Tamarkin et al. |
| 2005/0075407 | A1 | | 4/2005 | Tamarkin et al. |
| 2005/0191343 | A1 | | 9/2005 | Liang |
| 2005/0197407 | A1 | | 9/2005 | DiNardo et al. |
| 2005/0205086 | A1 | | 9/2005 | Tamarkin et al. |
| 2005/0232869 | A1 | | 10/2005 | Tamarkin et al. |
| 2005/0238597 | A1 | | 10/2005 | McCook et al. |
| 2005/0276842 | A1 | | 12/2005 | Zhang et al. |
| 2006/0057168 | A1 | * | 3/2006 | Larm et al. ..................... 424/400 |
| 2006/0193789 | A1 | | 8/2006 | Tamarkin et al. |
| 2006/0275218 | A1 | | 12/2006 | Tamarkin et al. |
| 2006/0292080 | A1 | | 12/2006 | Abram et al. |
| 2007/0110685 | A1 | | 5/2007 | Auspitz et al. |
| 2007/0134276 | A1 | | 6/2007 | Menegatti et al. |
| 2007/0189977 | A1 | | 8/2007 | Zhang et al. |
| 2007/0190043 | A1 | | 8/2007 | Sych et al. |
| 2007/0196323 | A1 | | 8/2007 | Zhang et al. |
| 2007/0196453 | A1 | | 8/2007 | Zhang et al. |
| 2007/0248658 | A1 | | 10/2007 | Zurdo Schroeder et al. |
| 2007/0280891 | A1 | | 12/2007 | Tamarkin et al. |
| 2007/0280972 | A1 | | 12/2007 | Zhang et al. |
| 2007/0292461 | A1 | | 12/2007 | Tamarkin et al. |

(Continued)

FOREIGN PATENT DOCUMENTS

| EP | 0832643 | 4/1998 |
| EP | 1958613 A1 | 8/2008 |
| JP | 2006-008700 A | 1/2006 |
| JP | 2007-503428 A | 2/2007 |
| JP | 2009-500382 A | 1/2009 |
| WO | WO 1997/031620 | 9/1997 |
| WO | WO 2004/037225 A2 | 5/2004 |
| WO | WO 2005/011567 A2 | 2/2005 |
| WO | WO 2006/024095 | 3/2006 |
| WO | WO 2006/040644 A2 | 4/2006 |

(Continued)

OTHER PUBLICATIONS

Remington's Pharmaceutical Sciences (17th Edition, Mack Publishing Company, Published 1985, p. 323).*

(Continued)

*Primary Examiner* — Alma Pipic
(74) *Attorney, Agent, or Firm* — Nath, Goldberg & Meyer; Joshua B. Goldberg; Scott H. Blackman

(57) ABSTRACT

The present invention relates to a novel oil in water emulsion aerosol foam composition containing an active agent for the treatment of various chronic and acute skin conditions, particularly acne and psoriasis; and processes for preparing the emulsion aerosol foam compositions. In particular, the present invention relates to oil in water emulsion aerosol foam compositions containing a retinoid in the oil phase.

28 Claims, 6 Drawing Sheets

(56) References Cited

U.S. PATENT DOCUMENTS

| | | |
|---|---|---|
| 2008/0044444 A1 | 2/2008 | Tamarkin et al. |
| 2008/0050317 A1 | 2/2008 | Tamarkin et al. |
| 2008/0063607 A1 | 3/2008 | Tamarkin et al. |
| 2008/0299220 A1 | 12/2008 | Tamarkin et al. |
| 2009/0041680 A1 | 2/2009 | Tamarkin et al. |
| 2012/0111352 A1* | 5/2012 | Wood et al. .................. 132/208 |

FOREIGN PATENT DOCUMENTS

| | | |
|---|---|---|
| WO | 2007/007198 * | 1/2007 |
| WO | WO 2007/007208 A2 | 1/2007 |
| WO | WO 2007/077029 A1 | 7/2007 |
| WO | WO 2007/082864 A2 | 7/2007 |
| WO | WO 2008/017914 A2 | 2/2008 |
| WO | WO 2008/057930 A2 | 5/2008 |
| WO | WO 2008/075207 A2 | 6/2008 |
| WO | WO 2008/104214 A1 | 9/2008 |
| WO | WO 2008/104215 A1 | 9/2008 |
| WO | WO 2008/148968 A1 | 12/2008 |
| WO | WO 2008/152444 A2 | 12/2008 |
| WO | WO 2009/029046 A1 | 3/2009 |

OTHER PUBLICATIONS

Liu (Water-Insoluble Drug Formulations, Second Edition, Published 2008, Edited by Rong Liu, pp. 215-216).*
English translation of Office Action dated Oct. 10, 2014, for corresponding JP application No. 2011-551371.

* cited by examiner

TOPICAL FOAM COMPOSITION

RELATED APPLICATIONS

This application is a continuation of application Ser. No. 12/711,337, filed 24 Feb. 2010, which claims the benefit of U.S. Provisional Application No. 61/202,403, filed 25 Feb. 2009, which are incorporated by reference in their entireties.

FIELD OF THE INVENTION

The present invention relates to novel aerosol foam compositions containing a pharmaceutically active agent for the treatment of skin disease.

BACKGROUND OF THE INVENTION

There are many challenges in topical drug delivery. The topical composition should deliver the active agent to the site of treatment, have desirable sensory characteristics, not leave an unpleasant residue on the surface of the skin, and not cause irritation or discomfort. Aerosol foams are known to be suitable for this purpose.

U.S. Pat. No. 7,387,807 to Callaghan et al. discloses a topical composition comprising an extract of feverfew, pharmaceutical excipients, cosmetic agents, and other biologically active substances, such as retinoids. The composition may be in the form of an emulsion such as a cream or lotion.

U.S. Pat. No. 7,326,408 to Angel et al. discloses a composition for the topical treatment of acne comprising one or more sunscreen agents and an antibacterial medication, where the composition may be in the form of a gel, spray, foam, lotion or other form suitable for application to the skin. The composition may further comprise an additional anti-acne medication, such as a retinoid (e.g. tretinoin, adapalene or tazarotene).

U.S. Pat. No. 6,730,288 to Abram describes an aerosol foam composition including an effective amount of a pharmaceutically active ingredient, an occlusive agent, an aqueous solvent, an organic cosolvent, the pharmaceutically active ingredient being insoluble in both water and the occlusive agent, and the occlusive agent being present in an amount sufficient to form an occlusive layer on the skin, in use.

US published application No. 2006/0292080 to Abram et al. describes an oil in water emulsion foam comprising: a vitamin or analogue thereof solubilized in the water phase and a stabilizer solubilized in the oil phase, an emulsifier, an occlusive agent, and an organic co-solvent, and no description of the particle size of the oil phase.

US published application No. 2006/0057168 to Larm et al. describes a process for the preparation of an oil in water microemulsion or sub-micron emulsion composition, in particular an oil in water microemulsion or sub-micron emulsion foam composition. These submicron or micro emulsion foams have a comparatively high oil content and require both a hydrophilic and a hydrophobic surfactant.

The present invention is directed to low oil and low surfactant submicron emulsions or microemulsion aerosol foams containing a pharmaceutically active agent, which are cosmetically elegant, chemically and physically stable, well tolerated, easy to formulate, and suitable for application to the face.

BRIEF SUMMARY OF THE INVENTION

The present invention is directed to an oil in water emulsion aerosol foam composition having an oil phase and a water phase, said composition comprising a pharmaceutically active agent, water, oil, an oil miscible organic solvent, a surfactant, and a propellant. The present invention provides for a low oil and a low surfactant content in an oil in water emulsion aerosol foam composition.

In one embodiment, the present invention provides an oil in water emulsion aerosol foam composition comprising an oil phase and a water phase, said composition comprising:
a pharmaceutically active agent,
water,
an oil present in an amount of less than about 10% by weight,
an oil miscible organic solvent,
a surfactant component comprising a hydrophilic surfactant, in an amount from about 0.1% to about 10% by weight, and
a propellant; and wherein the pharmaceutically active agent is solubilized in the oil phase of the composition, and wherein the particle size of the oil phase is less than about 1000 nm.

According to another embodiment, the present invention provides a process for the preparation of an oil in water submicron or micro emulsion aerosol foam composition, comprising a pharmaceutically active agent, water, an oil present in an amount of less than about 10% by weight, an oil miscible organic solvent, a surfactant component comprising a hydrophilic surfactant in an amount from about 0.1% to about 10% by weight, and a propellant, the process comprising:
a) admixing the pharmaceutically active agent, a first aliquot of water, oil, oil miscible organic solvent and surfactant component to form an oil in water emulsion,
b) heating the oil in water emulsion of step (a) to a phase inversion temperature wherein the oil in water emulsion forms a water in oil emulsion,
c) cooling the water in oil emulsion to below the phase inversion temperature to form a submicron or micro oil in water emulsion,
d) adding a second aliquot of water to cool the submicron or micro oil in water emulsion,
e) actuating a sample of the submicron or micro oil in water emulsion with a propellant to form an oil in water submicron or micro emulsion aerosol foam.

According to an embodiment, the present invention provides a product produced by this process.

According to a further embodiment, the present invention provides a method of treating a skin disease, disorder or condition, comprising administering to the skin of a patient requiring such treatment an effective amount of a composition of the present invention.

According to yet another embodiment, the present invention relates to the use of the compositions described herein for the preparation of a medicament for the treatment of a skin disease, disorder or condition.

DETAILED DESCRIPTION

Figure 1:
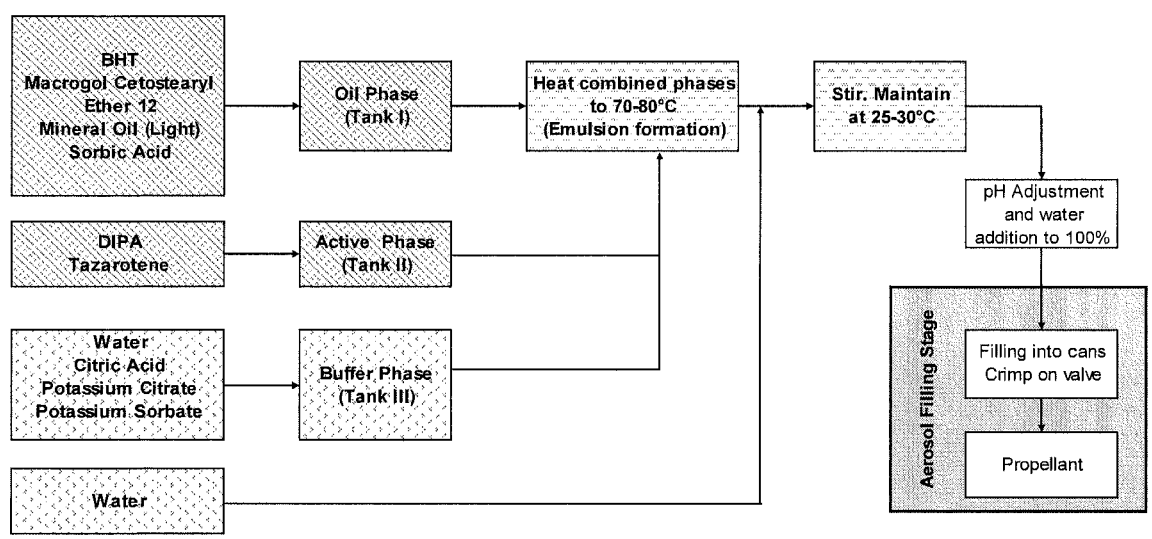
FIG. 1 is a schematic flow diagram showing one preferred embodiment of the present invention in which a low oil and low surfactant content, oil in water submicron or micro emulsion aerosol foam composition (730/2/1) is prepared. The method is described in detail in Example 1.

The present invention is directed to an oil in water emulsion aerosol foam composition having an oil phase and a water phase, said composition comprising a pharmaceutically active agent, water, oil, an oil miscible organic solvent, a surfactant, and a propellant. In an embodiment, the present invention provides low oil and low surfactant content, oil in water emulsion aerosol foam compositions. According to a further embodiment, the compositions are formulated as a submicron emulsion or microemulsion.

Thus, according to an embodiment, the present invention provides an oil in water emulsion aerosol foam composition comprising an oil phase and a water phase, said composition comprising:

a pharmaceutically active agent,
water,
an oil present in an amount of less than about 10% by weight,
an oil miscible organic solvent,
a surfactant component comprising a hydrophilic surfactant, in an amount from about 0.1% to about 10% by weight, and
a propellant; and wherein the pharmaceutically active agent is solubilized in the oil phase of the composition, and wherein the particle size of the oil phase is less than about 1000 nm.

Together, the oil and oil miscible organic solvent comprise the oil phase of the composition, along with any oil miscible excipients.

According to an embodiment, the mean particle size of the oil phase is about 100 nm.

In one embodiment, the present compositions are substantially free or free from a water miscible organic solvent, such as propylene glycol.

In one alternative embodiment, the pharmaceutically active agent is solubilized in the water phase of the composition.

The characteristics of oil particles in their delivery of pharmaceutically active agents across the skin barrier are summarised in Table 1 below:

TABLE 1

| Particle size | Description | Characteristics |
| --- | --- | --- |
| <10,000 nm | Emulsion | Blue-white, milky liquid, reasonable physical stability. Particles reside on skin surface → percutaneous delivery. |

TABLE 1-continued

| Particle size | Description | Characteristics |
| --- | --- | --- |
| 100-1000 nm | Submicron emulsion | Bluish, translucent liquid. Enhanced physical stability. Particles reside on skin surface → enhanced percutaneous delivery. |
| 10-100 nm | Microemulsion | Translucent-transparent liquid. Excellent physical stability. Particles reside on skin surface → enhanced percutaneous delivery. |
| 1-100 nm | Nanoemulsion | Translucent-transparent liquid. Excellent physical stability. Particles reside on skin surface, within stratum corneum and in hair follicles → optimal percutaneous delivery. |

Oil Component

Suitably, the oil is present in the composition in an amount from about 1% to about 9% by weight. In another embodiment the oil is present in an amount from about 3% to about 8% by weight, such as about 3%, 4%, 5%, 6%, 7% or 8% by weight.

The oil is in the discontinuous phase of the oil in water emulsion system. In an embodiment, the oil is a hydrocarbon. Suitably, the hydrocarbon is selected from an aromatic compound, or a linear, branched or cyclic alkane or alkene, or mixtures thereof.

According to an embodiment, the aromatic compound is selected from the group consisting of azulene, chamazulene and cyclohexylidene-diphenylmethane, and mixtures thereof.

According to a further embodiment, the linear, branched or cyclic alkane or alkene is selected from the group consisting of isoparaffin, didecene, diethylhexylcyclohexane, eicosane, isododecane, isoeicosane, isohexadecane, longifolene, mineral oil, paraffin, pentahydrosqualene, petrolatum, squalane, squalene, tetradecene, derivatives theoreof, and mixtures thereof.

According to an embodiment, the oil is mineral oil. In one embodiment, the mineral oil is present in an amount from about 1% to about 9% by weight. In another embodiment the mineral oil is present in about 3% to about 8% by weight, such as about 3%, 4%, 5%, 6%, 7% or 8% by weight.

In another embodiment, the oil is a vegetable oil. Suitably, the vegetable oil is selected from palm oil, soybean oil, rapeseed oil, sunflower oil, peanut oil, corn oil, olive oil, coconut oil, cottonseed oil, linseed oil, grapeseed oil, hazelnut oil or sesame oil, and mixtures thereof.

Surfactant Component

The present topical foam compositions comprise a surfactant component. Suitably, the surfactant is present in the composition in an amount from about 1% to about 8% by weight. In another embodiment the surfactant is present in an amount from about 2% to about 6% by weight, such as about 2%, 3%, 4%, 5% or 6% by weight.

A surfactant's hydrophilic/lipophilic balance (HLB) describes the surfactant's affinity toward water or oil. The HLB scale ranges from 1 (totally lipophilic) to 20 (totally hydrophilic), with 10 representing an equal balance of both characteristics. Lipophilic surfactants tend to form water-in-oil (w/o) emulsions, and hydrophilic surfactants tend to form oil-in-water (o/w) emulsions. The HLB of a blend of two surfactants equals the weight fraction of surfactant A times its HLB value plus the weight fraction of surfactant B times its HLB value (weighted average).

In one embodiment the surfactant component comprises a hydrophilic surfactant. In an another embodiment, the surfactant component consists of a single hydrophilic surfactant, and in another embodiment, the surfactant component comprises more than one surfactant and the weighted average of their HLB values is between about 10 and about 20. In another embodiment, the surfactant component consists of non-ionic surfactants.

Suitable non-ionic surfactants include but are not limited to ethoxylated fatty alcohol ethers, PEG derivatives, ethoxylated fatty acids, propylene glycol esters, fatty alcohols, glycerol esters and derivatives, polymeric ethers and sorbitan esters, and mixtures thereof.

Exemplary ethoxylated fatty alcohol ethers include steareth-2, steareth-10, steareth-20, ceteareth-2, ceteareth-3, ceteareth-5, ceteareth-6, ceteareth-10, ceteareth-12, ceteareth-15, ceteareth-20, ceteareth-21, ceteareth-22, ceteareth-25, ceteareth-30, ceteareth-31, ceteareth-32, ceteareth-33, laureth-3, laureth-4, laureth-5, laureth-9, laureth-10, laureth-12, laureth-15, laureth-20, laureth-21, laureth-22, laureth-23, nonoxynol-9, oleth-2, oleth-5, oleth-10 and oleth-20.

In one embodiment the hydrophilic ethoxylated fatty alcohol ether is selected from the group consisting of steareth-10, steareth-20, ceteareth-10, ceteareth-12, ceteareth-15, ceteareth-20, ceteareth-21, ceteareth-22, ceteareth-25, ceteareth-30, ceteareth-31, ceteareth-32, ceteareth-33, ceteareth-6, laureth-5, laureth-9, laureth-10, laureth-12, laureth-15, laureth-20, laureth-21, laureth-22, laureth-23, nonoxynol-9, oleth-10 and oleth-20.

In another embodiment the wherein the hydrophilic ethoxylated fatty alcohol ether is Macrogol Cetostearyl Ether 12 (ceteareth-12). In one embodiment the Macrogol Cetostearyl Ether 12 is present in the composition in an amount from about 1% to about 8% by weight. In another embodiment the Macrogol Cetostearyl Ether 12 is present in an amount from about 2% to about 6% by weight, such as about 2%, 3%, 4%, 5% or 6% by weight.

Exemplary PEG derivatives include PEG-7 hydrogenated castor oil, PEG-25 hydrogenated castor oil, PEG-30 castor oil, PEG-31 castor oil, PEG-32 castor oil, PEG-33 castor oil, PEG-34 castor oil, PEG-35 castor oil, PEG-40 hydrogenated castor oil, PEG-50 castor oil and PEG-60 hydrogenated castor oil.

Exemplary ethoxylated fatty acids include PEG-5 oleate, PEG-6 oleate, PEG-10 oleate, PEG-6 stearate, PEG-8 stearate and PEG-9 stearate, PEG-20 stearate, PEG-40 stearate, PEG-41 stearate, PEG-42 stearate, PEG-43 stearate, PEG-44 stearate, PEG-45 stearate, PEG-46 stearate, PEG-47 stearate, PEG-48 stearate, PEG-49 stearate, PEG-50 stearate and PEG-100 stearate.

Exemplary propylene glycol esters include propylene glycol palmitate and propylene glycol stearate.

Exemplary fatty alcohols include cetyl alcohol and stearyl alcohol.

Exemplary glyceryl esters and derivatives include glyceryl behenate, glyceryl dibehenate, glyceryl dioleate, glyceryl distearate, glyceryl linoleate, glyceryl oleate, glyceryl stearate, PEG-23 glyceryl cocoate, PEG-6 caprylic/capric glycerides, PEG-7 glyceryl cocoate, polyglyceryl-10 diisostearate, polyglyceryl-2 diisostearate, polyglyceryl-3 diisostearate and polyglyceryl-6 diisostearate.

Exemplary polymeric ethers include poloxamer 124, poloxamer 182, poloxamer 184, poloxamer 188, poloxamer 237, poloxamer 331, poloxamer 338 and poloxamer 407.

Exemplary sorbitan derivatives include polysorbate 20, polysorbate 40, polysorbate 60, polysorbate 80, sorbitan laurate, sorbitan oleate, sorbitan palmitate, sorbitan sesquioleate, sorbitan stearate and sorbitan trioleate.

In one embodiment, the surfactant component comprises one or more hydrophilic non-ionic surfactants and is substantially free, or free of lipophilic surfactant. According to an embodiment, the surfactant component is substantially free, or free of fatty alcohol.

In one embodiment, the surfactant component comprises a hydrophilic ethoxylated fatty alcohol ether. In another embodiment, the surfactant component comprises a hydrophilic ethoxylated fatty alcohol ether and is substantially free, or free of lipophilic surfactant.

Pharmaceutical Active Agent

Suitably, the pharmaceutically acceptable active agent for use in the compositions herein is selected from retinoids, retinoic acid metabolic blocking agents (RAMBAs), immune response modifier compounds, vitamin D analogues, corticosteroids, antihistamines, antibacterial agents, antifungal agents, antiviral agents, cytotoxic agents, psoralens, antialopecia agents, anti-androgens, antipruritic agents, keratolytic agents, tars, dithranol, antiseptics, sunscreens, anaesthetics, analgesics, skin conditioning agents and nutritional agents, salts thereof, derivatives thereof and mixtures thereof. In one embodiment, the compositions may comprise more than one pharmaceutically active agent, salt or derivative thereof. Suitable concentration ranges for the pharmaceutically active agent range from about 0.001% to about 30% by weight, depending on the nature of the active agent or combination of active agents.

In one embodiment, the pharmaceutically active agent is a retinoid. Examples of suitable retinoids include, but are not limited to, tazarotene, tretinoin, isotretinoin, acitretin, etretinate, adapalene, bexarotene, alitretinoin, retinol, retinal, retinyl palmitate, retinyl acetate, retinyl propionate, retinyl linoleate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol and 6-(2-(4,4-dimethylthiochroman-6-yl)-ethynyl) pyridine-3-carbaldehyde, salts thereof, derivatives thereof and mixtures thereof. In one embodiment, the retinoid is tazarotene. In an alternative embodiment, the retinoid is tretinoin. In another embodiment, the composition comprises a retinoid in combination with a second pharmaceutically active agent. In one embodiment the combination is tazarotene and a second pharmaceutically active agent. In another embodiment the combination is tretinoin and a second pharmaceutically active agent.

Suitably, one combination of the retinoid is with a corticosteroid, such as clobetasol propionate; or in combination with a vitamin D analogue such as calcipotriene; or in combination with an antibacterial such as clindamycin or a pharmaceutically acceptable salt thereof (e.g. clindamycin phosphate). Alternatively, in an embodiment, the present compositions comprise tretinoin in combination with an antibacterial agent, such as clindamycin or a pharmaceutically acceptable salt thereof (e.g. clindamycin phosphate).

Suitable concentration ranges for the retinoid in the composition include, for example, about 0.001% to about 5% by weight. In one embodiment the retinoid is present in an amount from about 0.01% to about 1%. In another embodiment the retinoid is present in an amount from about 0.025% to about 0.5%. In one embodiment when the retinoid is tazarotene, it is present in an amount from about 0.05% or 0.1% by weight. In another embodiment when the retinoid is tretinoin, it is present in an amount from about 0.025%, 0.05% or 0.1%.

A suitable retinoic acid metabolic blocking agents (RAMBAs) for use herein as a pharmaceutically acceptable active agent is rambazole.

Suitable immune response modifier compounds, immunosuppressant agents, immunoregulating agents and immunomodulators for use herein include chemically or biologically-derived agents that modify the immune response or the functioning of the immune system (by the stimulation of antibody formation or the inhibition of white blood cell activity). Exemplary agents or compounds include, but are not limited to cyclic peptides (such as cyclosporine), tacrolimus, tresperimus, pimecrolimus, sirolimius (rapamycin), verolimus, laflunimus, laquinimod, mycophenolic acid, and imidazoquinoline amines such as imiquimod, salts thereof, derivatives thereof, and mixtures thereof.

Suitable vitamin D analogues include, but are not limited to, calcidiol, calcitriol, calcipotriene, paricalcitol, 22-oxacolcitriol, dihydrotachysterol, calciferol, salts thereof, derivatives thereof, and mixtures thereof.

Suitable corticosteroids include, but are not limited to, alclometasone dipropionate, amcinonide, beclomethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone, fluprednidene acetate, flurandrenolide, flurandrenolone, fluticasone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, prednicarbate, salts thereof, derivatives thereof, and mixtures thereof.

Suitable antihistamines include, but are not limited to, cetirizine, vapitadine, diphenhydramine, triprolidine, pyrilamine, chlorcyclizine, promethazine, carbinoxamine, tripelennamine, brompheniramine, hydroxyzine, terfenadine, chlorpheniramine, salts thereof, derivatives thereof, and mixtures thereof.

Suitable antibacterial agents include, but are not limited to, gentamicin, neomycin, streptomycin, cefpodoxime proxetil, clindamycin, lincomycin, erythromycin, bacitracin, gramicidin(s), vancomycin, doxycycline, minocycline, oxytetracycline, tetracycline, fosfomycin, fusidic acid, mupirocin, sulfacetamide, metronidazole and dapsone, salts thereof, derivatives thereof, and mixtures thereof.

Suitable antifungal agents include, but are not limited to, those selected from the group consisting of echinocandins such as anidulafunin, caspofungin and micafungin; polyenes such as amphotericin B, candicidin, filipin, fungichromin, hachimycin, hamycin, lucensomycin, mepartricin, natamycin, nystatin, pecilocin, perimycin; allylamines such as butenafine, naftifine and terbinafine; imidazoles such as bifonazole, butoconazole, chlormidazole, cloconazole, clotrimazole, econazole, enilconazole, fenticonazole, flutrimazole, isoconazole, ketoconazole, lanoconazole, miconazole, neticonazole, omoconazole, oxiconazole nitrate, sertaconazole, sulconazole and tioconazole; thiocarbamates such as liranaftate, tolciclate, tolindate and tolnafate; triazoles such as albaconazole, fluconazole, itraconazole, posaconazole, ravuconazole, saperconazole, terconazole and voriconazole; and other antifungal agents such as acrisorcin, amorolfine, biphenamine, bromosalicylchloranilide, buclosamide, calcium propionate, chlorphenesin, ciclopirox, cloxyquin, coparaffinate, exalamide, flucytosine, haloprogin, hexetidine, loflucarban, nifuratel, potassium iodide, propionic acid, pyrithione, salicylanilide, sodium propionate, sulbentine, tenonitrozole, triacetin, undecylenic acid, zinc propionate, griseofulvin, oligomycins, pyrrolnitrin, siccanin, viridian, salts thereof, derivatives thereof, and mixtures thereof.

Suitable antivirals include, but are not limited to, acyclovir, desciclovir, carbovir, famciclovir, foscarnet sodium, ganciclovir, interferons, penciclovir, valaciclovir, salts thereof, derivatives thereof, and mixtures thereof.

Suitable cytotoxic agents include, but are not limited to, azathioprine, cyclophosphamide, cyclosporine, methotrexate, hydroxyurea, thalidomide, bleomycin, fluorouracil, salts thereof, derivatives thereof, and mixtures thereof.

An exemplary psoralen is methoxsalen.

Suitable anti-androgens include, but are not limited to, spironolactone, cyproterone, flutamide, finasteride, salts thereof, derivatives thereof, and mixtures thereof.

An exemplary antialopecia agent is minoxidil.

Suitable antipruritics include, but are not limited to, calamine, camphor and menthol, salts thereof, derivatives thereof, and mixtures thereof.

Suitable keratolytic agents include, but are not limited to, benzoyl peroxide, salicylic acid, urea, resorcinol, sulphur, salts thereof, derivatives thereof, and mixtures thereof.

Suitable tars include, but are not limited to, coal tar, pine tar, wood tar, salts thereof, derivatives thereof, and mixtures thereof.

Suitable antiseptics include, but are not limited to, hydrogen peroxide, chlorhexidine, cetrimide, povidone iodine, triclosan, salts thereof, derivatives thereof, and mixtures thereof.

Suitable sunscreens include, but are not limited to, aminobenzoic acid, avobenzone, bemotrizinol, bisoctrizole, β-carotene, cinoxate, 4-(dimethylamino)benzoic acid, dioxybenzone, drometrizole, ecamsule, ensulizole, ethylhexyl triazone, homosalate, lawsone, menthyl anthranilate, 4-methylbenzylidene camphor, mexenone, octabenzone, octocrylene, octyl methoxycinnamate, octyl salicylate, oxybenzone, sulisobenzone, zinc oxide, titanium dioxide, salts thereof, derivatives thereof, and mixtures thereof.

Suitable anaesthetics and analgesics include, but are not limited to, benzocaine, lidocaine, prilocalne and choline salicylate, salts thereof, derivatives thereof, and mixtures thereof.

Suitable skin-conditioning agents include, but are not limited to, hydrocarbon oils and waxes, silicones, fatty acid derivatives, cholesterol, di- and tri-glycerides, vegetable oils, acetoglyceride esters, alkyl esters, alkenyl esters, lanolin, milk tri-glycerides, wax esters, beeswax, sterols, phospholipids, derivatives thereof, and mixtures thereof.

Exemplary nutritional agents include vitamins, essential amino acids, essential fats, antioxidants, salts thereof, derivatives thereof, and mixtures thereof.

Water Phase

The topical foam compositions of the present invention also comprise water. Water forms the continuous phase of the emulsion system. In an embodiment, the foam compositions comprise water in an amount from about 65% to about 90% by weight. In another embodiment the water is present in an amount from about 70% to about 85% by weight. In another embodiment the water is present at about 77% by weight.

Oil Miscible Organic Solvent

The present topical foam compositions comprise an oil miscible organic solvent to facilitate solubilisation of the active agent in the oil. Together, the oil miscible organic solvent and oil comprise the oil phase of the composition.

The oil miscible organic solvent is present in the composition in an amount from about 1% to about 20% by weight.

In one embodiment the oil miscible organic solvent is present in an amount from about 3% to about 15% by weight. In another embodiment the oil miscible organic solvent is present in an amount of about 5% by weight.

Suitable, non-limiting examples of oil miscible organic solvents include alcohols such as caprylic alcohol, decyl alcohol, dodecylhexadecanol, dodecyltetradecanol, hexyl alcohol, hexyldecanol, hexyldecyloctadecanol, isocetyl alcohol, isostearyl alcohol, lauryl alcohol, myristyl alcohol, octyldecanol, octyldodecanol, oleyl alcohol, tridecyl alcohol; esters such as butyl stearate, C12-15 alkyl benzoate, C12-15 alkyl lactate, caprylic/capric triglyceride, cetearyl ethylhexanoate, cetearyl isononanoate, cetyl octanoate, cetyl palmitate, coco-caprylate/caprate, cocoglycerides, decyl oleate, dibutyl adipate, dicaprylyl carbonate, diethylhexyl adipate, di-ethylhexyl succinate, diisopropyl adipate, dioctyl malate, di-PPG-2 myreth-10 adipate, di-PPG-3 myristyl ether adipate, ethyl oleate, ethylhexyl cocoate, ethylhexyl hydroxystearate, ethylhexyl palmitate, ethylhexyl pelargonate, ethylhexyl stearate, hexyl laurate, hexyldecyl laurate, hexyldecyl stearate, isocetyl stearate, isocetyl stearoyl stearate, isodecyl oleate, isopropyl myristate, isopropyl palmitate, isostearyl neopentanoate, isotridecyl isononanoate, lauryl lactate, myristyl lactate, myristyl myristate, octyldodecyl stearoyl stearate, oleyl erucate, oleyl oleate, pentaerythrityl tetracaprylate/caprate, pentaerythrityl tetraisostearate, PPG-2 myristyl ether propionate, propylene glycol dicaprylate/dicaprate, propylene glycol isostearate, propylheptyl caprylate, stearyl octanoate; ethers such as dicaprylyl ether, PPG-10 cetyl ether, PPG-11 stearyl ether, PPG-14 butyl ether, PPG-15 stearyl ether, PPG-3 hydrogenated castor oil, PPG-3 myristyl ether; carboxylic acids such as C10-40 hydroxyalkyl acid, C10-40 isoalkyl acid, C32-36 isoalkyl acid, capric acid, caproic acid, caprylic acid, coconut acid, lauric acid, linoleic acid, linolenic acid, linseed acid, myristic acid, oleic acid, ricinoleic acid and lanolin.

According to an embodiment, the oil miscible organic solvent is selected from the group consisting of diisopropyl adipate, isopropyl myristate, dodecanol and caprylic/capric triglycerides.

In one embodiment, the oil miscible organic solvent is diisopropyl adipate (also referred to herein as DIPA). In one embodiment the DIPA is present in the composition in an amount from about 1% to about 20% by weight. In another embodiment the DIPA is present in an amount from about 3% to about 15% by weight. In another embodiment the DIPA is present in an amount of about 5% by weight.

According to a further embodiment, the present compositions comprise a second pharmaceutically acceptable active agent. In one embodiment, the second active agent is solubilized in the water phase (i.e. the continuous phase). This may be achieved by dissolving the second active agent in an aliquot of water or an aliquot of a water miscible organic solvent, and subsequently solubilising the aliquot in the composition.

According to an embodiment, the water miscible organic solvent is present in an amount from about 1% to about 20% by weight. According to a further embodiment, the water miscible organic solvent is present in an amount of about 10% by weight.

Suitably, water miscible organic solvents include, but are not limited to, alcohols, including amyl alcohol, benzyl alcohol, cyclohexanedimethanol, diacetone alcohol, ethyl alcohol, hexyl alcohol, isobutyl alcohol, isopropyl alcohol, methyl alcohol, n-butyl alcohol, propyl alcohol, t-butyl alcohol, tetrahydrofurfuryl alcohol; carboxylic acids, including acetic acid; diols, including 1,2-hexanediol, butylene glycol, diethylene glycol, dipropylene glycol, ethyl hexanediol, ethylene glycol, hexylene glycol, pentylene glycol, propylene glycol, tetraethylene glycol, triethylene glycol, tripropylene glycol; and polyols including polyethylene glycol, butanetriol, glycerol and 1,2,6-hexanetriol.

In one embodiment, the water miscible organic solvent is propylene glycol.

Propellant

It is recognized that the present topical foam compositions must utilize a propellant in order to produce the foam upon application. The propellant may be any suitable liquefied gas or mixture thereof, such as a hydrocarbon, a chlorofluorocarbon, dimethyl ether, hydrofluorocarbons and a mixture thereof.

Other suitable propellants include compressed gases such as nitrogen, carbon dioxide, nitrous oxide and air. In a preferred embodiment, the propellant is a mixture of hydrocarbons. In a further preferred embodiment, the mixture of hydrocarbons is a mixture of propane, n-butane and isobutane.

The propellant is present in an amount from about 1% to about 20% by weight, or about 3% to about 15% by weight. In one embodiment, the propellant is present in an amount from about 5% to about 10% by weight, such as about 5%, 6%, 7%, 8%, 9% or 10% by weight. The propellant may be introduced into the composition at the time of filling, utilizing a pressurized container such as a standard aerosol dispenser.

When the composition is released from the pressurized container, the composition is an aerosol foam (also known as a mousse). According to one embodiment, the aerosol foam is homogeneous. In another embodiment, the aerosol foam breaks easily with shear, such as gentle mechanical action e.g. rubbing or spreading.

In another embodiment the propellant is absent from the composition. According to such an embodiment, the composition may be expelled from its container by mechanical means, such as by a pump action or a squeezing action on the container.

Suitable pressurized containers for use herein include aluminium, tin-plate and glass containers.

In one embodiment, the pressurized container is a one-piece aluminium container in which the inner surface is lined with a chemically inert lining. One suitable inner surface lining for use herein is polyamide-imide (PAM), such as that supplied by Exal Corporation, of Youngstown, Ohio. The container may be fitted with an upright-use or inverted-use valve and a conventional foam spout actuator. Alternatively, the container may be fitted with a metered-dose valve.

Dermatologically Acceptable Excipients

According to an embodiment, the compositions may further comprise one or more dermatologically acceptable excipients. Non-limiting examples of such dermatologically acceptable excipients include diluents, suspending agents, adjuvants, preservatives, colorants, emollients, pH adjusting agents (including buffers), thickeners, humectants, fragrances, stabilizers, chelating agents, anticaking agents, viscosity increasing agents, solubilizers, plasticizers, penetration enhancing agents, film forming agents, antioxidants, wetting agents, foam boosters or any mixture of these components.

In one embodiment, the one or more dermatologically acceptable excipients comprise a preservative, an antioxidant and a pH adjusting agent.

Preservative

The present topical aerosol foam compositions may additionally comprise a preservative. The preservative is present in the composition in an amount from about 0.01% to about 2% by weight. In one embodiment the preservative is present in an amount from about 0.1% to about 1% by weight. In another embodiment the preservative is present in an amount of about 0.3% by weight.

Suitable preservatives include, but are not limited to benzyl alcohol, diazolidinyl urea, methyl paraben, ethyl paraben, propyl paraben, butyl paraben, phenoxyethanol, sorbic acid and salts thereof such as potassium sorbate, benzoic acid and salts thereof such as sodium benzoate, and mixtures thereof.

According to an embodiment, the preservative is a combination of sorbic acid and potassium sorbate.

Antioxidant

The present topical aerosol foam compositions may further comprise an antioxidant. The antioxidant is present in the composition in an amount from about 0.001% to about 1% by weight. In one embodiment the antioxidant is present from about 0.05% to about 0.5% by weight. In another embodiment the antioxidant is present in an amount of about 0.1% by weight.

Suitable antioxidants include, but are not limited to, butylated hydroxytoluene (BHT), butylated hydroxyanisole, tocopherol, propyl gallate, vitamin E TPGS, derivatives thereof, and mixtures thereof. In one embodiment, the antioxidant is BHT.

pH Adjusting Agent

The present topical aerosol foam compositions may further comprise a pH adjusting agent to aid in stabilizing the active agent. According to an embodiment, the pH adjusting agent is present in an amount from about 0.01% to about 10% by weight. In one embodiment, the pH adjusting agent is a base. Suitable pH adjusting bases include but are not limited to bicarbonates, carbonates and hydroxides (such as alkali or alkaline earth metal hydroxides, as well as transition metal hydroxides). The pH adjusting agent may also be an acid, an acid salt, or mixtures thereof. The pH adjusting agent may also be a buffer. Suitable buffers include, but are not limited to citrate/citric acid, acetate/acetic acid, phosphate/phosphoric acid, formate/formic acid, propionate/propionic acid, lactate/lactic acid, carbonate/carbonic acid, ammonium/ammonia, edentate/edetic acid, derivatives thereof, and combinations thereof. According to an embodiment, the pH adjusting agent is a citrate/citric acid buffer. According to an embodiment, the citrate/citric acid buffer is present in an amount from about 0.02% to about 2% by weight.

In another embodiment, the present invention relates to an oil in water emulsion aerosol foam composition comprising: tazarotene, water, an oil in an amount from about 3% to about 8% by weight, an oil miscible organic solvent, a surfactant component comprising a non-ionic hydrophilic surfactant in an amount from about 2% to about 6% by weight, and a hydrocarbon propellant, wherein the tazarotene is solubilized in the oil phase of the composition and wherein the particle size of the oil phase is less than about 1000 nm.

According to an embodiment, the mean particle size of the oil phase of the tazarotene aerosol foam is about 100 nm.

The tazarotene foam formulation exemplified by these embodiments is particularly suited for application to small regions of the face for the treatment of acne. In one embodiment, the tazarotene aerosol foam formulation is dispensed from a metered dose actuator. In another alternative embodiment, the tazarotene aerosol foam composition is formulated as a macro emulsion (i.e. the particle size of the oil phase is greater than 1000 nm).

In another embodiment, a second pharmaceutically active agent is solubilized in the composition. In another embodiment the second pharmaceutically active agent is solubilized in the water phase of the composition. This may be achieved by dissolving the further pharmaceutically active agent in an aliquot of water which is subsequently solubilized in the composition. Alternatively, the second pharmaceutically active agent is dissolved in an aliquot of water miscible organic solvent which is subsequently solubilized in the composition. In another embodiment the second pharmaceutically active agent is in a composition comprising the retinoid tazarotene.

Definitions

As used herein, the terms "administering" and "administered," refer to any method which delivers the composition to a subject in such a manner as to provide a therapeutic effect.

As used herein, the term "derivative(s) thereof" refers to prodrugs, solvates, hydrates, esters and acids of the pharmaceutically active agent.

As used herein, the phrase an "effective amount" of an active agent or ingredient, or pharmaceutically active agent or ingredient, which are synonymous herein, refers to an amount of the pharmaceutically active agent sufficient to have a therapeutic effect upon administration. An effective amount of the active agent may, will, or is expected to cause relief of symptoms. Effective amounts of the active agent will vary with the particular disease or diseases being treated, the severity of the disease, the duration of the treatment, and the specific components of the composition being used.

As used herein, the term "fatty alcohol" refers to an alcohol having an aliphatic chain from about 9 to about 22 carbon atoms long.

As used herein, an "emulsion" refers to a mixture of two or more immiscible (unblendable) liquids wherein the particle size of the dispersed phase (i.e. oil in the case of an oil in water emulsion) is less than about 10,000 nm.

As used herein, a "submicron emulsion" refers to a mixture of two or more immiscible (unblendable) liquids wherein the particle size of the dispersed phase (i.e. oil in the case of an oil in water emulsion) is in the range from about 100 nm to about 1000 nm.

As used herein, a "microemulsion" refers to a mixture of two or more immiscible (unblendable) liquids wherein the particle size of the dispersed phase (i.e. oil in the case of an oil in water emulsion) is in the range from about 10 nm to about 100 nm.

As used herein, "nanoemulsion" refers to a mixture of two or more immiscible (unblendable) liquids wherein the particle size of the dispersed phase (i.e. oil in the case of an oil in water emulsion) is in the range from about 1 nm to 100 nm.

As used herein, the term "phase inversion temperature" refers to a temperature where an oil in water emulsion inverts to a water in oil emulsion (or vice versa).

As used herein, a "pH adjusting agent" refers to a specific pH adjusting agent or agents, including but not limited to, a buffer, a base or an acid, salts thereof and mixtures thereof, added to a composition.

The phrase "dermatologically acceptable excipient" as used herein refers to any inactive ingredient present in the herein described compositions.

As used herein, the phrase "pharmaceutically acceptable salts" refers to salts that are pharmaceutically acceptable and that possess the desired pharmacological activity of the parent compound. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion, or an aluminium ion; or (ii) protonates an organic base such as, for example, ethanolamine, diethanolamine, triethanolamine, tromethamine and N-methylglucamine.

As used herein, a "subject", "individual" or "patient" refers to any subject, particularly a human, for whom therapy is desired.

As used herein, a "treatment" or "treating" of a disease, disorder or condition encompasses alleviation of at least one symptom thereof, a reduction in the severity thereof, or the delay, prevention or inhibition of the progression thereof. Treatment need not mean that the disease, disorder or condition is totally cured. A useful composition herein need only to reduce the severity of a disease, disorder or condition, reduce the severity of symptoms associated therewith, provide improvement to a patient's quality of life, or delay, prevent or inhibit the onset of a disease, disorder or condition.

Any concentration range, percentage range or ratio range recited herein is to be understood to include concentrations, percentages or ratios of any integer within that range and fractions thereof, such as one tenth and one hundredth of an integer, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

Throughout the application, descriptions of various embodiments use "comprising" language, however in some specific instances, an embodiment can alternatively be described using the language "consisting essentially of" or "consisting of".

For the purposes of better understanding the present teachings and in no way limiting their scope, unless otherwise indicated, all numbers expressing quantities, percentages or proportions, and other numerical values used in the specification and claims, are to be understood as being modified in all instances by the term "about."

As used herein, the term "substantially free" of a specified component refers to a composition with less than about 1% of the specified component.

Other terms used herein are intended to be defined by their well-known meanings in the art.

Process of Preparation

In one embodiment, the present invention provides a process for the preparation of an oil in water submicron or micro emulsion aerosol foam composition, comprising a pharmaceutically active agent, water, an oil present in an amount of less than about 10% by weight, an oil miscible organic solvent, a surfactant component comprising a hydrophilic surfactant in an amount from about 0.1% to about 10% by weight, and a propellant, the process comprising:

a) admixing the pharmaceutically active agent, a first aliquot of water, oil, oil miscible organic solvent and surfactant component to form an oil in water emulsion, b) heating the oil in water emulsion of step (a) to a phase inversion temperature wherein the oil in water emulsion forms a water in oil emulsion, c) cooling the water in oil emulsion to below the phase inversion temperature to form a submicron or micro oil in water emulsion, d) adding a second aliquot of water to cool the submicron or micro oil in water emulsion, e) actuating a sample of the submicron or micro oil in water emulsion with a propellant to form an oil in water submicron or micro emulsion aerosol foam.

According to an embodiment, the first aliquot of water comprises about 10% to about 40% by weight of the total water content of the submicron or micro oil in water emulsion aerosol foam and the second aliquot of water comprises about 90% to about 60% by weight of the total water content of the submicron or micro oil in water emulsion aerosol foam.

According to an embodiment, the first aliquot of water comprises about 10% to about 40% by weight of the total water content of the submicron or micro oil in water emulsion aerosol foam and the second aliquot of water comprises about 90% to about 60% by weight of the total water content of the submicron or micro oil in water emulsion aerosol foam.

According to another embodiment, the first aliquot of water comprises about 15% to about 35% of the total water content of the submicron or micro oil in water emulsion aerosol foam and the second aliquot of water comprises about 85% to about 65% of the total water content of the submicron or micro oil in water emulsion aerosol foam.

According to a further embodiment, the first aliquot of water comprises about 20% to about 30% of the total water content of the submicron or micro oil in water emulsion aerosol foam and the second aliquot of water comprises about 80% to about 70% of the total water content of the submicron or micro oil in water emulsion aerosol foam.

According to yet a further embodiment, the first aliquot of water comprises about 25% of the total water content of the submicron or micro oil in water emulsion aerosol foam and the second aliquot of water comprises about 75% of the total water content of the submicron or micro oil in water emulsion aerosol foam.

The presently described process provides for the preparation of a low oil and low surfactant submicron or micro emulsion aerosol foam, where a concentrated submicron or micro emulsion is prepared (comprising the first aliquot of water) and is subsequently diluted (with the second aliquot of water) to ultimately afford the desired low oil and low surfactant submicron or micro emulsion. By initially preparing a concentrated submicron or micro emulsion, a sufficient concentration of surfactant is present in the composition to stabilize the submicron or micro sized oil phase. The dilution step then provides the desired low oil and low surfactant submicron or micro emulsion. It is thought that the addition of the second aliquot of water (which is at a temperature substantially below the phase inversion temperature) serves to fix the submicron or micro emulsion structure of the composition and, of course, dilutes the composition to provide the low oil and low surfactant composition.

According to an embodiment, a second pharmaceutically active agent is solubilized in the water phase of the composition. This may be achieved by dissolving the second pharmaceutically active agent in an aliquot of water or water miscible organic solvent, which is subsequently solubilized in the composition.

In one embodiment, the second pharmaceutically active agent dissolved in an aliquot of water or water miscible organic solvent is added to the submicron or micro oil in water emulsion following step (d)). That is, the second pharmaceutically active agent is solubilized in the water phase of the composition after formation of the submicron or micro emulsion.

Another aspect of the invention is the product produced by this process.

Methods of Treatment

The emulsion aerosol foam compositions of the present invention are cosmetically elegant and suitable for application to the face for treating a skin disorder or condition. The compositions are easily spread, non-greasy, non-drying and leave minimal residue on the skin.

The present invention provides for a method of treating a skin disease, disorder or condition, comprising administering to the skin of a patient requiring such treatment an effective amount of a composition of the present invention. In one embodiment, the skin disease, disorder or condition is acne. In another embodiment, the skin disease, disorder or condition is psoriasis.

The present invention also relates to the use of the compositions as described herein for the preparation of a medicament for the treatment of a skin disease, disorder or condition.

The present invention also relates to a method of treating a skin disease, disorder or condition by administering to the skin of a patient requiring such treatment an effective amount of a composition of the present invention.

Exemplary, non-limiting, skin diseases, disorders or conditions treatable by the present compositions include acne, rosacea, dermatitis, psoriasis and fungal disorders. According to an embodiment, the skin disease, disorder or condition is acne. According to another embodiment, the skin disease, disorder or condition is psoriasis.

In an embodiment, the present compositions are used in combination with a suitable additional pharmaceutical dosage form. The additional pharmaceutical dosage form is administered to a patient either prior to, concomitantly with, or after the compositions described herein.

In one embodiment in this regard, the present composition and the additional pharmaceutical dosage form are administered to a patient at the same time. In an alternative embodiment, one of the present compositions and the additional pharmaceutical dosage form is administered in the morning and the other is administered in the evening.

In another embodiment, the additional pharmaceutical dosage form can be a suitable oral pharmaceutical. In this regard, the present composition can be applied to the target area of the patient, prior to, concomitantly with, or after ingestion of the oral medication.

According to an embodiment, the present composition comprises a retinoid and the oral pharmaceutical dosage form comprises a pharmaceutically active agent selected from the group consisting of an antibiotic, a contraceptive, a retinoid such as isotretioin, and a nutritional agent.

Furthermore, the foam compositions of the present invention may be used with other adjunct therapies and treatments, such as pre-washing with soaps or cleansers. However, care is needed in this regard, since antibacterial soaps and abrasive soaps may increase irritation.

EXAMPLES

The following examples are illustrative of preferred embodiments herein and are not to be construed as limiting the present invention thereto. All percentages are based on the percent by weight of the final delivery system or formulation prepared, unless otherwise indicated and all totals equal 100% by weight.

Tables 2a, 2b, 2c and 2d

Oil in Water Submicron/Micro Emulsion Foam Formulations—Tazarotene (0.1%)

TABLE 2a

| 706/8/2 - absent propellant* | |
|---|---|
| Component | % w/w |
| BHT | 0.10 |
| Macrogol Cetostearyl Ether 12 (Ceteareth 12) | 5.00 |
| Light Mineral Oil | 6.00 |
| Sorbic Acid | 0.40 |
| DIPA | 5.00 |
| Tazarotene | 0.10 |
| Citric Acid Anhydrous | 0.03 |
| Potassium Citrate Monohydrate | 0.57 |
| Deionized Water | 82.80 |
| Total | 100.000 |

TABLE 2b

| 706/8/3 - absent propellant* | |
|---|---|
| Component | % w/w |
| BHT | 0.10 |
| Macrogol Cetostearyl Ether 12 (Ceteareth 12) | 5.00 |
| Light Mineral Oil | 8.00 |
| Sorbic Acid | 0.40 |
| DIPA | 7.00 |
| Tazarotene | 0.10 |
| Citric Acid Anhydrous | 0.03 |
| Potassium Citrate Monohydrate | 0.54 |
| Deionized Water | 78.83 |
| Total | 100.000 |

*The formulations described in Tables 2a & 2b were dispensed as a foam following the addition of approximately 7 to 8 grams of AP70 propellant per 100 grams of aerosol base.

TABLE 2c

| 730/2/1 | | | |
|---|---|---|---|
| Component | Function | % w/w | % w/w |
| BHT | Antioxidant | 0.100 | 0.093 |
| Macrogol Cetostearyl Ether 12 (Ceteareth 12) | Surfactant | 5.000 | 4.635 |
| Light Mineral Oil | Oil | 6.000 | 5.562 |
| Sorbic Acid | Preservative | 0.150 | 0.139 |
| Potassium Sorbate | Preservative | 0.200 | 0.185 |
| Diisopropyl adipate | Organic Solvent | 5.000 | 4.635 |

TABLE 2c-continued

730/2/1

| Component | Function | % w/w | % w/w |
|---|---|---|---|
| Tazarotene | Active ingredient | 0.100 | 0.093 |
| Citric Acid Anhydrous | Buffer | 0.037 | 0.034 |
| Potassium Citrate Monohydrate | Buffer | 0.103 | 0.096 |
| Deionized Water | Water | 83.310 | 77.228 |
| Propellant AP70 (propane, butane & isobutane) | Propellant | — | 7.300 |
| Total | | 100.000 | 100.000 |

TABLE 2d

SF10260-02

| Component | Function | % w/w | % w/w |
|---|---|---|---|
| BHT | Antioxidant | 0.100 | 0.093 |
| Macrogol Cetostearyl Ether 12 (Ceteareth 12) | Surfactant | 5.000 | 4.648 |
| Light Mineral Oil | Oil | 6.000 | 5.578 |
| Sorbic Acid | Preservative | 0.150 | 0.139 |
| Potassium Sorbate | Preservative | 0.200 | 0.186 |
| Diisopropyl adipate | Organic Solvent | 5.000 | 4.648 |
| Tazarotene | Active ingredient | 0.100 | 0.093 |
| Citric Acid Anhydrous | Buffer | 0.037 | 0.034 |
| Potassium Citrate Monohydrate | Buffer | 0.103 | 0.096 |
| Deionized Water | Water | 83.310 | 77.445 |
| Propellant AP70 (propane, butane & isobutane) | Propellant | — | 7.040 |
| Total | | 100.000 | 100.000 |

Example 1

Method of Preparing Submicron/Micro Emulsion Foam Formulation—Tazarotene

Procedure: aerosol base production (730/2/1):
  Phase 1 (Oil phase): BHT, ceteareth-12, mineral oil and sorbic acid
  Phase 2 (Active phase): tazarotene dissolved in diisopropyl adipate (DIPA)
  Phase 3 (Buffer phase): deionized water (about 22.8% of the total water content of aerosol base), citric acid, potassium citrate and potassium sorbate
  Phase 4 (Water phase): deionized water (about 77.2% of the total water content of aerosol base)

1. Dissolve tazarotene in diisopropyl adipate in a suitable stainless steel container at ambient temperature (Phase 2).
2. Prepare buffer solution at ambient temperature in a stainless steel container (Phase 3).
3. Add oil phase ingredients to the main batch vessel (Phase 1).
4. Combine Phase 1, Phase 2 and Phase 3 in the main batch vessel. Commence low heating with stirring. Continue heating to the phase inversion temperature range of 70° C. to 80° C. until a water in oil emulsion occurs.
5. Commence cooling to below the phase inversion temperature. When the emulsion becomes an oil in water submicron/micro emulsion, add ambient temperature Phase 4 deionized water at a moderate rate. Stir until uniform. Maintain batch at 25° C.-30° C.
6. Test pH of the aerosol base.
7. Adjust pH to a range of 4.70 to 5.50 with 1N potassium hydroxide solution or with 10% citric acid solution.
8. Adjust to 100% with deionized water (to account for evaporative water loss). The abovementioned procedure is represented in schematic form in FIG. 1.

Alternative Procedure—Aerosol Base Production (SfW0260-02):

At ambient temperature, dissolve tazarotene in diisopropyl adipate in a side vessel, while stirring.

Add mineral oil and BHT to the side vessel, while stirring until the solution is homogenous.

At ambient temperature, add deionized water (about 28.8% of total water content of aerosol base), citric acid and potassium citrate to a main batch vessel, while stirring until all components are fully dissolved.

Add potassium sorbate to the main batch vessel, while stirring until the potassium sorbate is fully dissolved.

Continue to stir the contents of the main batch vessel and add the contents of the side vessel (tazarotene, DIPA, mineral oil and BHT) to the main batch vessel, followed by addition of sorbic acid and ceteareth-12.

Commence heating and continue heating until the phase inversion temperature is reached i.e. where the oil in water emulsion inverts to a water in oil emulsion (as measured by conductivity or visual observation). The phase inversion temperature is in the range of about 70° C. to about 80° C.

Cool the main batch vessel to below the phase inversion temperature (approximately 69° C.) to facilitate the formation of an oil in water submicron/micro emulsion.

Add ambient temperature deionized water (about 71.2% of total water content of aerosol base). Continue stirring and maintain main batch vessel at around 25° C.-30° C.

Test the pH and adjust as necessary to a range of 4.70 to 5.50. Adjust with deionized water to account for evaporative water loss.

Aerosol Filling and Crimping

The aerosol base is filled into suitable aluminium aerosol containers, suitable valves are inserted, vacuum crimped and gassed with a suitable propellant.

TABLE 3

Submicron/micro emulsion foam - tazarotene (0.1%) plus calcipotriene (0.005%)

| Item | Ingredient | Function | % w/w |
|---|---|---|---|
| | First active phase | | |
| 1 | Diisopropyl adipate | Organic solvent | 5.000 |
| 2 | Tazarotene | Active ingredient | 0.100 |
| | Hydrocarbon oil phase | | |
| 3 | BHT | Antioxidant | 0.100 |
| 4 | Macrogol Cetostearyl Ether 12 (Ceteareth 12) | Surfactant | 5.000 |
| 5 | Mineral oil (light) | Hydrocarbon | 6.000 |
| 6 | Tocopherol | Antioxidant | 0.002 |
| | First water phase | | |
| 7 | Water (deionized) | Aqueous solvent | 19.000 |
| 8 | EDTA, Na$_2$ | Buffer | 0.060 |
| 9 | Disodium phosphate | Buffer | 0.080 |

TABLE 3-continued

Submicron/micro emulsion foam - tazarotene (0.1%) plus calcipotriene (0.005%)

| | Ingredient | Function | % w/w |
|---|---|---|---|
| | Second water phase | | |
| 10 | Water (deionized) | Aqueous solvent | 54.653 |
| | Second active phase | | |
| 11 | Propylene glycol | Organic solvent | 10.000 |
| 12 | Calcipotriene | Active ingredient | 0.005 |
| | Total | | 100.000 |
| Items | Finished product | | |
| 1 to 12 | Aerosol base | Concentrate | 92.7 |
| 13 | Hydrocarbon propellant AP70 | Propellant | 7.3 |
| | Total | | 100.0 |

Example 2

Method of Preparing Submicron/Micro Emulsion Foam—Tazarotene (0.1%) Plus Calcipotriene (0.005%)

Aerosol Base:
1. Add BHT (Item 3), ceteareth-12 (Item 4), mineral oil (Item 5) and tocopherol (Item 6) to the main mixing vessel.
2. Prepare the First active phase by adding diisopropyl adipate (Item 1) and tazarotene (Item 2) to a small mixing vessel and mix until tazarotene has dissolved.
3. Add the First active phase solution (Items 1 and 2) to the main mixing vessel.
4. Into a separate mixing vessel prepare First water phase by adding water (Item 7).
5. Start stirring First water phase and add EDTA, Na$_2$ (Item 8) and disodium phosphate (Item 9) to water and mix until dissolved.
6. Add First water phase (Items 7 to 9) to the main mixing vessel.
7. While monitoring the conductivity of the contents of the main mixing vessel (Items 1 to 9) commence heating, to approximately 80° C., and start stirring.
8. As the temperature increases the mixture inverts from an oil in water emulsion to a water in oil emulsion and a corresponding decrease in the conductivity is observed.
9. When the temperature reaches approximately 80° C. stop heating and commence slow cooling of the contents of the main mixing vessel while maintaining stirring.
10. At approximately 70° C. the mixture inverts from a water in oil emulsion to an oil in water emulsion and a corresponding increase in the conductivity is observed. The appearance of the mixture also changes from opaque to translucent.
11. At this temperature, when the mixture is translucent, add the Second water phase (Item 10), at ambient temperature, to the main mixing vessel and continue stirring. The temperature of the mixture will decrease to approximately 40° C. following the addition of the Second water phase.
12. While stirring the mixture, continue cooling until the temperature range decreases to approximately 25° C. to 30° C.
13. Prepare the Second active phase by adding propylene glycol (Item 11) and calcipotriene (Item 12) to a small mixing vessel and mix until calcipotriene has dissolved.
14. Transfer the Second active phase (Items 11 and 12) to the main mixing vessel and stir until the mixture is uniform.

Finished Product:
1. Add Aerosol base (Items 1 to 12) to an empty aerosol container.
2. Secure an aerosol valve onto the aerosol container.
3. Add Propellant (Item 13) to the aerosol container.
4. Test the aerosol container to confirm that there is no leakage.
5. Place an actuator onto the aerosol valve.
6. Shake the aerosol container prior to dispensing at room temperature.

TABLE 4

Submicron/micro emulsion foam - clindamycin phosphate (1%) plus tretinoin (0.05%)

| Item | Ingredient | Function | % w/w |
|---|---|---|---|
| | First active phase | | |
| 1 | Diisopropyl adipate | Organic solvent | 10.000 |
| 2 | Tretinoin | Active ingredient | 0.050 |
| | Hydrocarbon oil phase | | |
| 3 | BHT | Antioxidant | 0.100 |
| 4 | Macrogol Cetostearyl Ether 12 (Ceteareth 12) | Surfactant | 5.000 |
| 5 | Mineral oil (light) | Hydrocarbon | 6.000 |
| | First water phase | | |
| 6 | Water (deionized) | Aqueous solvent | 22.000 |
| 7 | Anhydrous citric acid | Buffer | 0.037 |
| 8 | Potassium citrate monohydrate | Buffer | 0.103 |
| | Second water phase | | |
| 9 | Water (deionized) | Aqueous solvent | 32.960 |
| | Second active phase | | |
| 10 | Water (deionized) | Aqueous solvent | 20.000 |
| 11 | Clindamycin phosphate (80% active) | Active ingredient | 1.250 |
| | Preservative phase | | |
| 12 | Propylene glycol | | 2.000 |
| 13 | Benzyl alcohol | | 0.500 |
| | Total | | 100.000 |
| Items | Finished product | | |
| 1 to 13 | Aerosol base | Concentrate | 91.1 |
| 14 | Hydrocarbon propellant AP70 | Propellant | 8.9 |
| | Total | | 100.0 |

Example 3

Method of Preparing Submicron/Micro Emulsion Foam Formulation—Clindamycin Phosphate (1%) Plus Tretinoin (0.05%)

Aerosol Base:
1. Add BHT (Item 3), ceteareth-12 (Item 4) and mineral oil (Item 5) to the main mixing vessel.
2. Prepare the First active phase by adding (Item 1) and tretinoin (Item 2) to a small mixing vessel and mix until dissolved.

3. Add the First active phase solution (Items 1 and 2) to the main mixing vessel.
4. Into a separate mixing vessel prepare First water phase by adding water (Item 6).
5. Start stirring First water phase and add anhydrous citric acid (Item 7) and potassium citrate monohydrate (Item 8) to water and mix until dissolved.
6. Add First water phase (Items 6 to 8) to the main mixing vessel.
7. While monitoring the conductivity of the contents of the main mixing vessel (Items 1 to 8) commence heating, to approximately 80° C., and start stirring.
8. As the temperature increases the mixture inverts from an oil in water emulsion to a water in oil emulsion and a corresponding decrease in the conductivity is observed.
9. After the mixture inverts from an oil in water emulsion to a water in oil emulsion stop heating and commence slow cooling of the contents of the main mixing vessel while maintaining stirring.
10. With cooling, the mixture inverts from a water in oil emulsion back to an oil in water emulsion and a corresponding increase in the conductivity is observed. The appearance of the mixture also changes from opaque to translucent.
11. At this temperature, when the mixture is translucent, add the Second water phase (Item 9), at ambient temperature, to the main mixing vessel and continue stirring. The temperature of the mixture will decrease following the addition of the Second water phase.
12. While stirring the mixture, continue cooling until the temperature range decreases to approximately 25° C. to 30° C.
13. Prepare the Second active phase by adding water (Item 10) and clindamycin phosphate (Item 11) to a small mixing vessel and mix until clindamycin phosphate has dissolved.
14. Transfer the Second active phase (Items 10 and 11) to the main mixing vessel and stir until the mixture is uniform.
15. Prepare the Preservative phase by adding propylene glycol (Item 12) and benzyl alcohol (Item 13) to a small mixing vessel and mix until uniform.
16. Transfer the Preservative phase (Items 12 and 13) to the main mixing vessel and stir until the mixture is uniform.

Finished Product:
1. Add Aerosol base (Items 1 to 13) to an empty aerosol container.
2. Secure an aerosol valve onto the aerosol container.
3. Add Propellant (Item 14) to the aerosol container.
4. Test the aerosol container to confirm that there is no leakage.
5. Place an actuator onto the aerosol valve.
6. Shake the aerosol container prior to dispensing at room temperature.

The formulations described in tables 5 to 9 are further illustrative of the present invention.

TABLE 5

Submicron/micro emulsion foam - tazarotene (0.1%) plus clobetasol propionate (0.05%)

| Item | Ingredient | Function | % w/w |
|---|---|---|---|
| | First active phase | | |
| 1 | Diisopropyl adipate | Organic solvent | 5.000 |
| 2 | Tazarotene | Active ingredient | 0.100 |
| | Hydrocarbon oil phase | | |
| 3 | BHT | Antioxidant | 0.100 |
| 4 | Macrogol Cetostearyl Ether 12 (Ceteareth 12) | Surfactant | 5.000 |
| 5 | Mineral oil (light) | Hydrocarbon | 2.000 |
| 6 | Sorbic acid | Preservative | 0.200 |
| 7 | Petrolatum | Hydrocarbon | 2.000 |
| | First water phase | | |
| 8 | Water (deionized) | Aqueous solvent | 22.030 |
| 9 | Anhydrous citric acid | Buffer | 0.040 |
| 10 | Potassium citrate monohydrate | Buffer | 0.100 |
| 11 | Potassium sorbate | Preservative | 0.270 |
| | Second water phase | | |
| 12 | Water (deionized) | Aqueous solvent | 53.110 |
| | Second active phase | | |
| 13 | Propylene glycol | Organic solvent | 10.000 |
| 14 | Clobetasol propionate | Active ingredient | 0.050 |
| | Total | | 100.000 |
| Items | Finished product | | |
| 1 to 14 | Aerosol base | Concentrate | 92.7 |
| 15 | Hydrocarbon propellant AP70 | Propellant | 7.3 |
| | Total | | 100.0 |

TABLE 6

Submicron/micro emulsion foam - Vitamin D3 (0.02%)

| Item | Ingredient | Function | % w/w |
|---|---|---|---|
| | Active phase | | |
| 1 | Diisopropyl adipate | Organic solvent | 2.000 |
| 2 | Vitamin D3 | Active ingredient | 0.020 |
| | Hydrocarbon oil phase | | |
| 3 | Macrogol Cetostearyl Ether 12 (Ceteareth 12) | Surfactant | 3.000 |
| 4 | Mineral oil (light) | Oil | 3.000 |
| 5 | Tocopherol | Antioxidant | 0.002 |
| | First water phase | | |
| 6 | Water (deionized) | Aqueous solvent | 10.000 |
| 7 | Citric acid | Buffer | q.s. |
| 8 | Potassium citrate | Buffer | q.s. |
| | Second water phase | | |
| 9 | Water (deionized) | Aqueous solvent | to 100.000 |
| 10 | Methyl paraben | Preservative | q.s. |
| | Total | | 100.000 |
| Items | Finished product | | |
| 1 to 10 | Aerosol base | Concentrate | 92.7 |
| 11 | Hydrocarbon propellant AP70 | Propellant | 7.3 |
| | Total | | 100.0 |

TABLE 7

Submicron/micro emulsion foam - Salicylic acid (2%)

| Ingredient | Function | % w/w |
|---|---|---|
| Item | Active phase | |
| 1 Diisopropyl adipate | Organic solvent | 9.000 |
| 2 Salicylic acid | Active ingredient | 2.000 |
| Hydrocarbon oil phase | | |
| 3 Macrogol Cetostearyl Ether 12 (Ceteareth 12) | Surfactant | 6.000 |
| 4 Mineral oil (light) | Oil | 8.000 |
| First water phase | | |
| 5 Water (deionized) | Aqueous solvent | 26.000 |
| 6 Citric acid | Buffer | q.s. |
| 7 Potassium citrate | Buffer | q.s. |
| Second water phase | | |
| 8 Water (deionized) | Aqueous solvent | to 100.000 |
| 9 Benzyl alcohol | Preservative | q.s. |
| Total | | 100.000 |
| Items | Finished product | |
| 1 to 9 Aerosol base | Concentrate | 92.7 |
| 10 Hydrocarbon propellant AP70 | Propellant | 7.3 |
| Total | | 100.0 |

TABLE 8

Submicron/micro emulsion foam - Adapalene 0.1%

| Ingredient | Function | % w/w |
|---|---|---|
| Item | Active phase | |
| 1 Diisopropyl adipate | Organic solvent | 3.000 |
| 2 Adapalene | Active ingredient | 0.100 |
| Hydrocarbon oil phase | | |
| 3 BHT | Antioxidant | 0.100 |
| 4 Macrogol Cetostearyl Ether 20 (Ceteareth 20) | Surfactant | 3.000 |
| 5 Mineral oil (light) | Oil | 4.000 |
| First water phase | | |
| 6 Water (deionized) | Aqueous solvent | 15.000 |
| 7 Citric acid | Buffer | q.s. |
| 8 Potassium citrate | Buffer | q.s. |
| Second water phase | | |
| 9 Water (deionized) | Aqueous solvent | to 100.000 |
| 10 Benzyl alcohol | Preservative | q.s. |
| Total | | 100.000 |
| Items | Finished product | |
| 1 to 9 Aerosol base | Concentrate | 92.7 |
| 10 Hydrocarbon propellant AP70 | Propellant | 7.3 |
| Total | | 100.0 |

TABLE 9

Submicron/micro emulsion foam - clobetasol propionate (0.05%)

| Ingredient | Function | % w/w |
|---|---|---|
| Item | Active phase | |
| 1 Diisopropyl adipate | Organic solvent | 5.00 |
| 2 Clobetasol propionate | Active ingredient | 0.05 |
| Hydrocarbon oil phase | | |
| 3 Macrogol Cetostearyl Ether 20 (Ceteareth 20) | Surfactant | 5.00 |
| 4 Mineral oil (light) | Oil | 5.00 |
| 5 BHT | Antioxidant | 0.10 |
| First water phase | | |
| 6 Water (deionized) | Water | 20.00 |
| 7 Citric acid | Buffer | q.s. |
| 8 Potassium citrate | Buffer | q.s. |
| Second water phase | | |
| 9 Water (deionized) | Water | to 100% |
| 10 Methyl paraben | Preservative | q.s. |
| Total | | 100.00 |
| Items | Finished product | |
| 1 to 10 Aerosol base | Concentrate | 92.7 |
| 11 Hydrocarbon propellant AP70 | Propellant | 7.3 |
| Total | | 100.0 |

Example 4

Skin Penetration Study

A skin penetration study was performed, comparing the topical delivery of the tazarotene submicron/micro emulsion foam (base) formulations of Examples 2a and 2b to TAZORAC™ cream and gel formulations using in-vitro skin distribution assays.

Split-thickness skin (~0.50 mm) sections were mounted in flow-through diffusion cells and test agents were applied at a finite dose of 15.63 mg/cm$^2$ on 3 skin donors with 5 replicates each.

The tissues were collected at various time points (t=0, 2, 6 hrs), washed, tape stripped, and split into epidermis and dermis. The distribution of tazarotene within the epidermis, dermis, and wash were quantified by LC/MS/MS with a 50 pg/mL LOQ.

Figure 2:
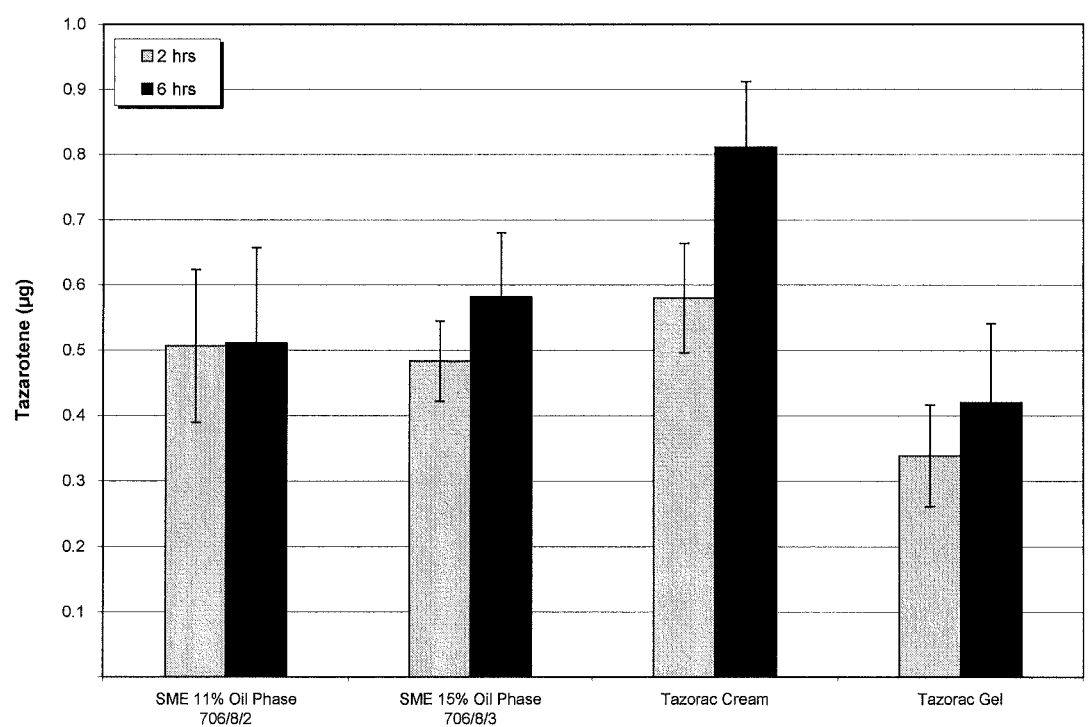
FIG. 2 shows the distribution of tazarotene within the epidermis after application of tazarotene formulations of the present invention (706/8/2 and 706/8/3) compared to commercially available tazarotene cream and gel formulations (i.e. TAZORAC® cream and gel).
Figure 3:
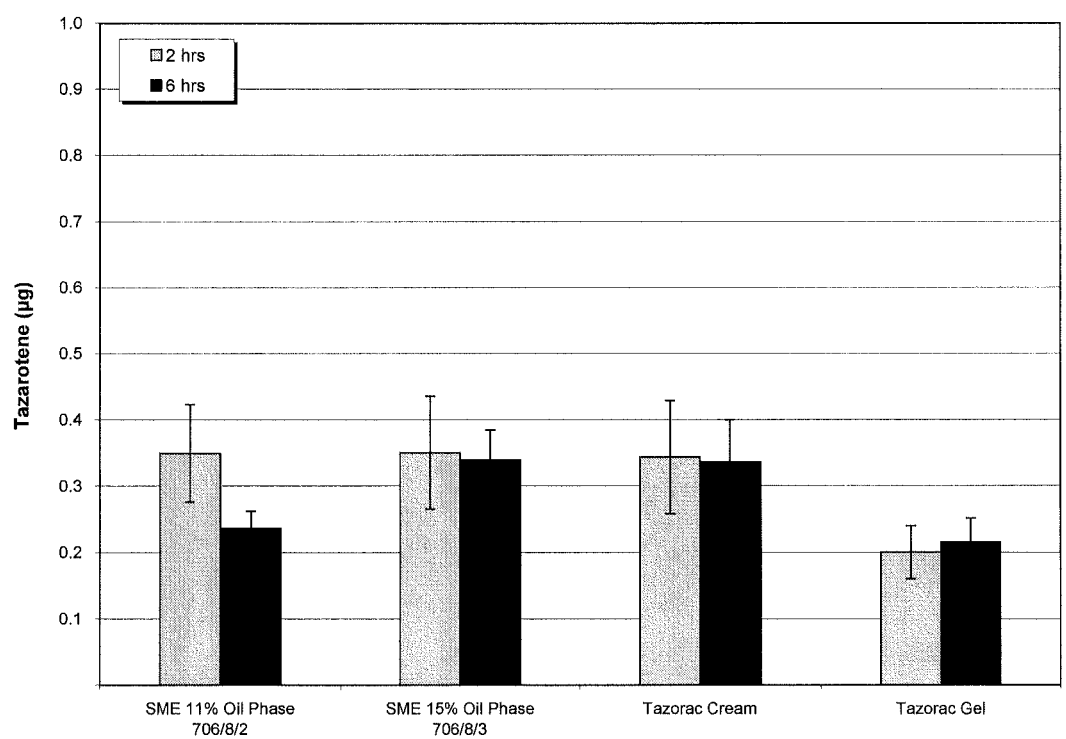
FIG. 3 shows the distribution of tazarotene within the dermis after application of tazarotene formulations of the present invention (706/8/2 and 706/8/3) compared to commercially available tazarotene cream and gel formulations (i.e. TAZORAC® cream and gel).

As shown in FIGS. 2 and 3, the skin penetration of the tazarotene foam (base) formulations in the epidermis and dermis was similar to the commercial comparators (i.e. TAZORAC® cream and gel).

Example 5

Compatibility of Surfactants with Tazarotene

Figure 4:
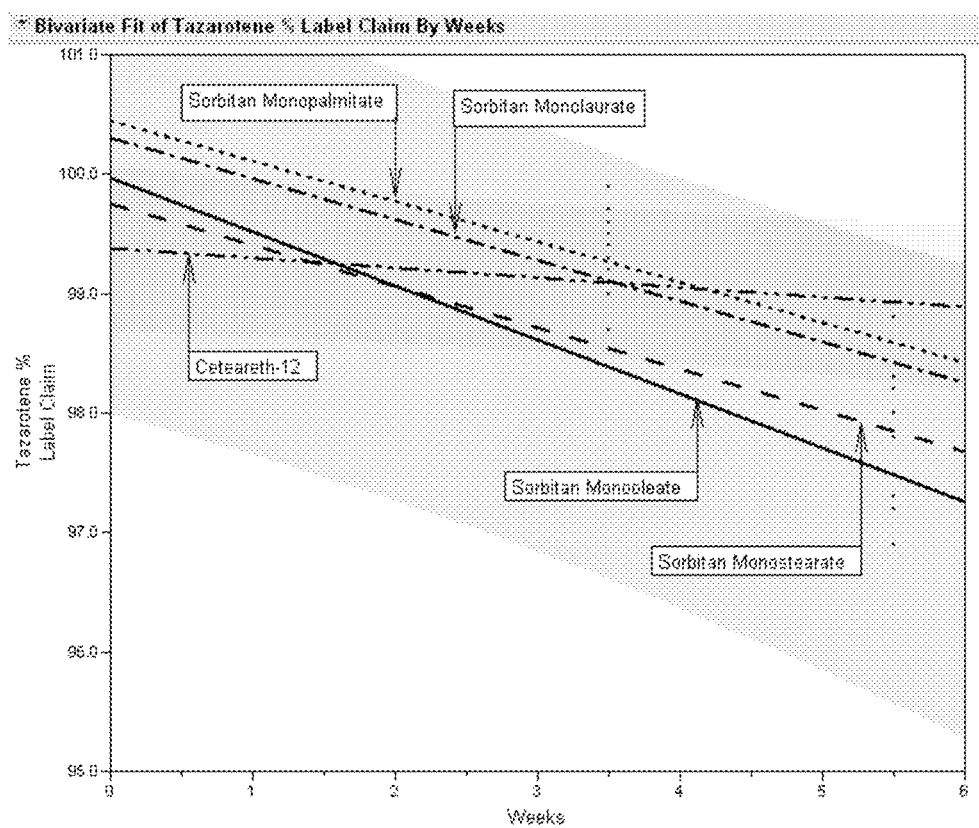
FIG. 4 shows the compatibility of high HLB ethoxylated fatty alcohol ether surfactant with tazarotene (tazarotene stability). A comparison is made against various low HLB surfactants.
Figure 5:
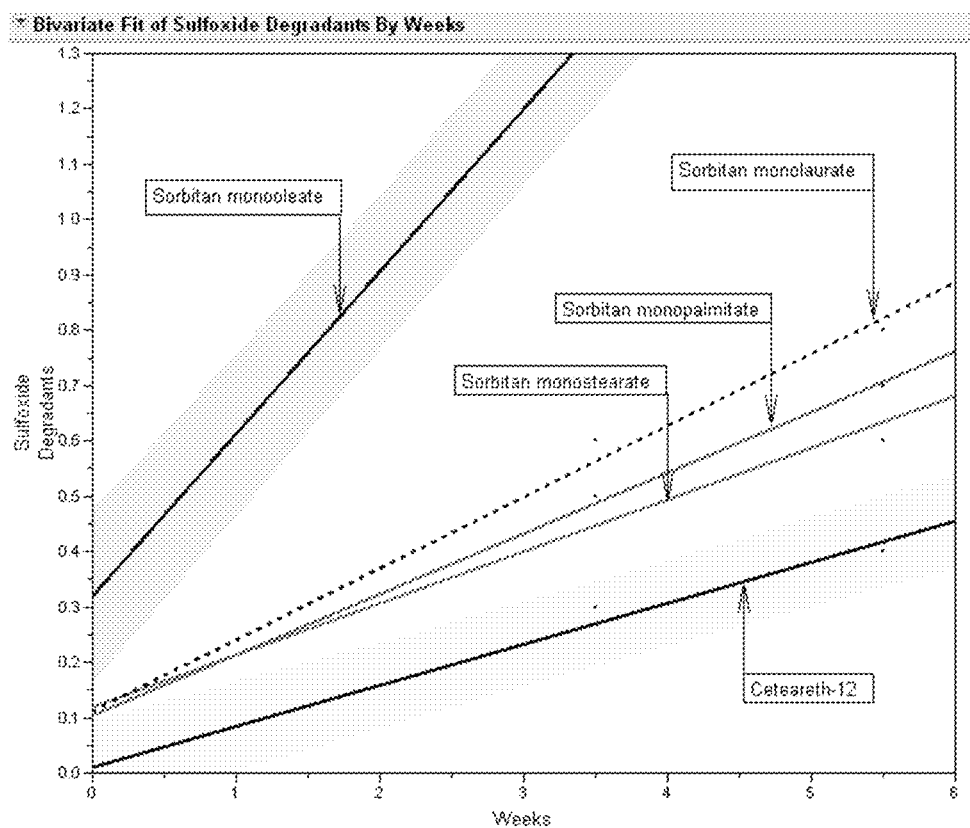
FIG. 5 shows the compatibility of high HLB ethoxylated fatty alcohol ether surfactant with tazarotene (tazarotene sulfoxide formation). A comparison is made against various low HLB surfactants.

An accelerated stability study (using HPLC) was conducted at 50° C. to measure the compatibility of tazarotene with various surfactants. FIGS. 4 and 5 show that tazarotene was most stable in a hydrophilic ethoxylated fatty alcohol ether surfactant, such as Ceteareth—12, in contrast to various lipophilic surfactants.

Example 6

Measurement of Particle Size Distribution

Figure 6:
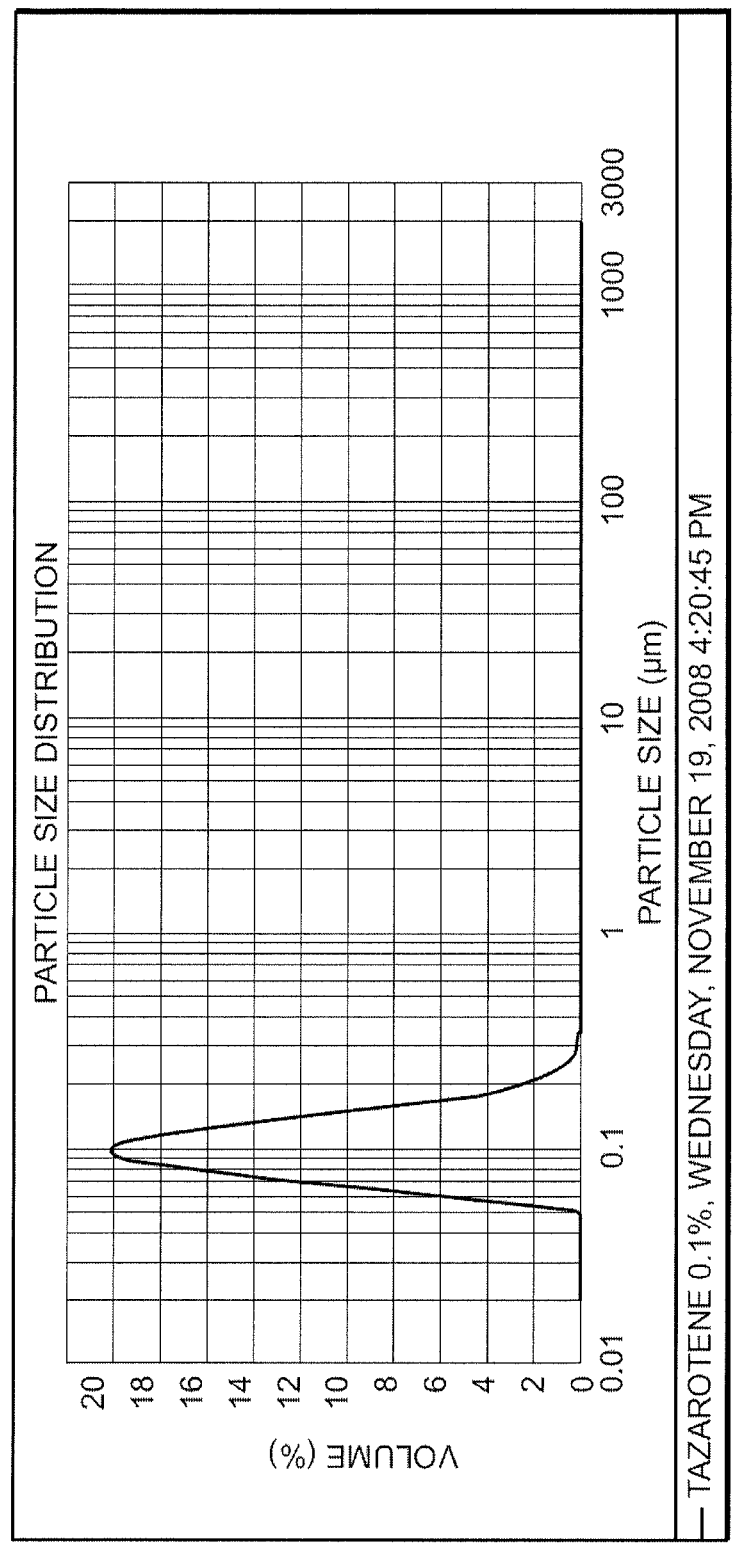
FIG. 6 shows the particle size distribution of the oil phase of the present submicron or micro emulsions (730/2/1).

The particle size distribution of the oil phase of the submicron/micro emulsions (aerosol foam base) of the present invention was measured using a Malvern Mastersizer 2000 instrument. FIG. 6 illustrates the particle size distribution of the oil phase of a preferred formulation (730/2/1). The mean particle size was 0.097 μm, that is, about 0.1 μm (i.e. about 100 nm).

What is claimed is:

1. An oil in water emulsion aerosol foam composition comprising an oil phase and a water phase, said composition comprising:
   i) tazarotene,
   ii) water in an amount from about 65% to about 90% by weight,
   iii) an oil present in an amount from about 1% to about 10% by weight, wherein the oil is selected from the group consisting of azulene, chamazulene, isoparaffin, linear alpha olefins, cyclohexlidenediphenyl methane, didecene, diethylhexylcyclohexane, eicosane, isododecane, isoeicosane, isohexadecane, longifolene, mineral oil, light mineral oil, paraffin, pentahydrosqualene, petrolatum squalane, squalene, tetradecene, and mixtures thereof,
   iv) an oil miscible organic solvent selected from the group consisting of diisopropyl adipate, isopropyl myristate, octyl dodecanol and caprylic/capric triglyceride, and mixtures thereof,
   v) a surfactant component comprising a sufficient and effective amount of a hydrophilic ethoxylated fatty alcohol ether regardless of whether any other surfactant is present, in an amount from about 1% to about 8% by weight, and
   vi) a propellant comprising one or more hydrocarbon propellants;
   wherein the surfactant component is selected from the group consisting of steareth-10, ceteareth-12, oleth-10, and mixtures thereof, and
   wherein the tazarotene is solubilized in the oil phase of the composition, and the particle size of the oil phase is less than about 1000 nm, and wherein all percentages are based on the total weight of the composition.

2. The aerosol foam composition according to claim 1, wherein the composition comprises water in an amount from about 70% to about 85% by weight.

3. The aerosol foam composition according to claim 1, wherein the oil is present in an amount from about 1% to about 9% by weight.

4. The aerosol foam composition according to claim 3, wherein the oil is present in an amount from about 3% to about 8% by weight.

5. The aerosol foam composition according to claim 4, wherein the oil is mineral oil.

6. The aerosol foam composition according to claim 1, wherein the oil is mineral oil.

7. The aerosol foam composition according to claim 1, wherein the surfactant component is present in an amount from about 2% to about 6% by weight.

8. A method of treating a skin disease, disorder or condition, comprising administering to the skin of a patient requiring such treatment an effective amount of a composition according to claim 1.

9. An oil in water emulsion aerosol foam composition comprising an oil phase and a water phase, said composition comprising:
   i) tazarotene;
   ii) water in an amount from about 70% to about 85% by weight;
   iii) an oil selected from the group consisting of azulene, chamazulene, isoparaffin, linear alpha olefins, cyclohexlidenediphenyl methane, didecene, diethylhexylcyclohexane, eicosane, isododecane, isoeicosane, isohexadecane, longifolene, mineral oil, light mineral oil, paraffin, pentahydrosqualene, petrolatum, squalane, squalene, tetradecene, and mixtures thereof; and
   wherein the oil is present in an amount from about 3% to about 8% by weight;
   iv) an oil miscible organic solvent selected from the group consisting of diisopropyl adipate, isopropyl myristate, octyl dodecanol and caprylic/capric triglyceride, and mixtures thereof;
   v) a sufficient and effective amount of a non-ionic surfactant component comprising a hydrophilic ethoxylated fatty alcohol ether regardless of whether any other surfactant is present, in an amount from about 2% to about 6% by weight;
   vi) a hydrocarbon propellant;
   wherein the non-ionic surfactant component is selected from the group consisting of steareth-10, ceteareth-12 oleth-10, and mixtures thereof, and
   wherein the tazarotene is solubilized in the oil phase of the composition, and the particle size of the oil phase is less than about 1000 nm, and wherein all percentages are based on the total weight of the composition.

10. A method of treating a skin disease, disorder or condition, comprising administering to the skin of a patient requiring such treatment an effective amount of a composition according to claim 9.

11. A process for the preparation of an oil in water submicron or micro emulsion aerosol foam composition, comprising tazarotene, water, an oil present in an amount of less than about 10% by weight, an oil miscible organic solvent, a surfactant component comprising a hydrophilic surfactant in an amount from about 0.1% to about 10% by weight, and a propellant, the process comprising:
   a. admixing the tazarotene, a first aliquot of water, oil, oil miscible organic solvent and surfactant component to form an oil in water emulsion,
   b. heating the oil in water emulsion of step (a) to a phase inversion temperature wherein the oil in water emulsion forms a water in oil emulsion,
   c. cooling the water in oil emulsion to below the phase inversion temperature to form a submicron or micro oil in water emulsion,
   d. adding a second aliquot of water to cool the submicron or micro oil in water emulsion, and
   e. actuating a sample of the submicron or micro oil in water emulsion with a propellant to form an oil in water submicron or micro emulsion aerosol foam.

12. The process according to claim 11, wherein the first aliquot of water comprises about 10% to about 40% by weight of the total water content of the submicron or micro emulsion aerosol foam and the second aliquot of water comprises about 90% to about 60% by weight of the total water content of the submicron or micro emulsion aerosol foam.

13. The aerosol foam composition according to claim 9, wherein the oil is mineral oil.

14. The aerosol foam composition according to claim 13, wherein the oil miscible organic solvent is diisopropyl adipate.

15. The aerosol foam composition according to claim 9, wherein the hydrophilic ethoxylated fatty alcohol ether is ceteareth-12.

16. The aerosol foam composition according to claim 1, wherein the oil miscible organic solvent is present in an amount from about 3% to about 15% by weight.

17. The aerosol foam composition according to claim 1, further comprising an antioxidant.

18. The aerosol foam composition according to claim 17, wherein the antioxidant is selected from the group consisting of butylated hydroxytoluene, butylated hydroxyanisole, tocopherol, propyl gallate, polyethylene glycol succinate, and mixtures thereof.

19. The aerosol foam composition according to claim 18, wherein the antioxidant is butylated hydroxytoluene.

20. The aerosol foam composition according to claim 17, wherein the antioxidant is present in an amount from about 0.05% to about 0.5% by weight.

21. The aerosol foam composition according to claim 1, wherein the propellant is present in an amount from about 5% to about 10% by weight.

22. The aerosol foam composition according to claim 1, further comprising a preservative.

23. The aerosol foam composition according to claim 22, wherein the preservative is selected from the group consisting of benzyl alcohol, diazolidinyl urea, methyl paraben, ethyl paraben, propyl paraben, butyl paraben, phenoxyethanol, sorbic acid, benzoic acid, salts thereof, and mixtures thereof.

24. The aerosol foam composition according to claim 23, wherein the preservative is sorbic acid or a salt thereof.

25. The aerosol foam composition according to claim 1, further comprising a pH adjusting agent.

26. The aerosol foam composition according to claim 25, wherein the pH adjusting agent is a buffer selected from the group consisting of citrate/citric acid, acetate/acetic acid, phosphate/phosphoric acid, formate/formic acid, propionate/propionic acid, lactate/lactic acid, carbonate/carbonic acid, ammonium/ammonia, edentate/edetic acid, and combinations thereof.

27. The aerosol foam composition according to claim 25, wherein the buffer is citrate/citric acid.

28. The aerosol foam composition according to claim 25, wherein the pH of the composition is adjusted to a pH in the range of from 4.70 to 5.50.

* * * * *

UNITED STATES PATENT AND TRADEMARK OFFICE
CERTIFICATE OF CORRECTION

PATENT NO. : 10,688,071 B2
APPLICATION NO. : 13/553036
DATED : June 23, 2020
INVENTOR(S) : Leon Loupenok It is certified that error appears in the above-identified patent and that said Letters Patent is hereby corrected as shown below:

In the Claims

Claim 1, Column 25, Line 24, please delete "octyl dodecanol and caprylic/capric triglycerdie, and mixtures thereof" and replace with "octyl dodecanol, caprylic/capric triglyceride, and mixtures thereof".

Claim 1, Column 25, Line 26, please delete "v) a surfactant component comprising a sufficient and effective amount of a hydrophilic ethoxylated fatty alcohol ether regardless of whether any other surfactant is present, in an amount from about 1% to about 8% by weight, and vi) a propellant comprising one or more hydrocarbon propellants; wherein the surfactant component is selected from the group consisting of steareth-10, ceteareth-12, oleth-10, and mixtures thereof" and replace with "v) a surfactant component comprising from about 1% to about 8% by weight of a hydrophilic ethoxylated fatty alcohol ether selected from the group consisting of steareth-10, ceteareth-12, oleth-10, and mixtures thereof, and vi) a propellant comprising one or more hydrocarbon propellants; and".

Claim 9, Column 26, Line 10, please delete "octyl dodecanol and carprylic/capric triglyceride" and replace with "octyl dodecanol, caprylic/capric triglyceride".

Claim 9, Column 26, Line 12, please delete "v) a sufficient and effective amount of a non-ionic surfactant component comprising a hydrophilic ethoxylated fatty alcohol ether regardless of whether any other surfactant is present, in an amount from about 2% to about 6% by weight; vi) a hydrocarbon propellant; wherein the non-iconic surfactant component is selected from the group consisting of steareth-10, ceteareth-12 oleth-10, and mixtures thereof, and" and replace with "v) a non-ionic surfactant component comprising from about 2% to about 6% by a weight of a hydrophilic ethoxylated fatty alcohol ether selected from the group consisting of steareth-10, ceteareth-12, oleth-10, and mixtures thereof, and vi) a hydrocarbon propellant, and".

Please delete Claim 11, Column 26, Lines 29-49, and replace with "A method of making an oil in water submicron emulsion aerosol foam composition comprising: a) admixing tazarotene, a first aliquot of water, an oil, an oil miscible organic solvent, and a surfactant component to form an oil in Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,688,071 B2 water emulsion, b) heating the oil in water emulsion of step a) to a phase inversion temperature wherein the oil in water emulsion forms a water in oil emulsion, c) cooling the water in oil emulsion to below the phase inversion temperature to form a submicron oil in water emulsion, d) adding a second aliquot of water to cool the submicron oil in water emulsion, and e) actuating the submicron oil in water emulsion with a propellant to form the oil in water submicron emulsion aerosol foam; wherein the oil in water submicron emulsion aerosol foam comprises i) tazarotene, ii) water in an amount from about 65% to about 90% by weight, iii) an oil in an amount from about 1% to about 10% by weight, wherein the oil is selected from the group consisting of azulene, chamazulene, isoparaffin, linear alpha olefins, cyclohexlidenediphenyl methane, didecene, diethylhexylcyclohexane, eicosane, isododecane, isoeicosane, isohexadecane, longifolene, mineral oil, light mineral oil, paraffin, pentahydrosqualane, petrolatum, squalene, squalane, tetradecene, and mixtures thereof, iv) an oil miscible organic solvent selected from the group consisting of diisopropyl adipate, isopropyl myristate, octyl dodecanol, carprylic/capric triglyceride, and mixtures thereof; v) a surfactant component comprising from about 1% to about 8% by weight of a hydrophilic ethoxylated fatty alcohol ether selected from the group consisting of steareth-10, ceteareth-12, oleth-10, and mixtures thereof, and vi) a propellant comprising one or more hydrocarbon propellants; and wherein the tazarotene is solubilized in the oil phase of the composition, and the particle size of the oil phase is less than about 1000 nm, and wherein all percentages are based on the total weight of the composition".

Claim 12, Column 26, Line 52, please delete "or micro emulsion" and replace with "emulsion".

Claim 12, Column 26, Line 55, please delete "or micro emulsion" and replace with "emulsion".

Claim 28, Column 28, Line 18, please delete "wherein the pH of the composition is adjusted to a pH in the range of from 4.70 to 5.50" and replace with "wherein the pH of the composition is from 4.70 to 5.50".